United States Patent
Rowley Grant et al.

(10) Patent No.: US 10,489,907 B2
(45) Date of Patent: Nov. 26, 2019

(54) ARTIFACT IDENTIFICATION AND/OR CORRECTION FOR MEDICAL IMAGING

(71) Applicant: Siemens Healthcare GmbH, Erlangen (DE)

(72) Inventors: Katharine Lynn Rowley Grant, Rochester, MN (US); Bernhard Schmidt, Furth (DE)

(73) Assignee: Siemens Healthcare GmbH, Erlangen (DE)

( * ) Notice: Subject to any disclaimer, the term of this patent is extended or adjusted under 35 U.S.C. 154(b) by 204 days.

(21) Appl. No.: 15/810,694

(22) Filed: Nov. 13, 2017

(65) Prior Publication Data
US 2019/0147588 A1 May 16, 2019

(51) Int. Cl.
| | | |
|---|---|---|
| G06K 9/00 | (2006.01) | |
| G06T 7/00 | (2017.01) | |
| G06T 5/50 | (2006.01) | |
| G06T 11/00 | (2006.01) | |
| G16H 30/40 | (2018.01) | |

(Continued)

(52) U.S. Cl.
CPC ............ G06T 7/0012 (2013.01); G06T 5/002 (2013.01); G06T 5/50 (2013.01); G06T 11/008 (2013.01); G16H 30/40 (2018.01); G06T 2207/10081 (2013.01); G06T 2207/10088 (2013.01); G06T 2207/10104 (2013.01); G06T 2207/10108 (2013.01); G06T 2207/10132 (2013.01); G06T 2207/20076 (2013.01); G06T 2207/20081 (2013.01); G06T 2207/20084 (2013.01);

(Continued)

(58) Field of Classification Search
CPC ......... G06T 7/0012; G06T 5/002; G06T 5/50; G06T 11/008; G06T 2210/41; G06T 2207/10081; G06T 2207/10088; G06T 2207/10104; G06T 2207/10108; G06T 2207/10132; G06T 2207/20076; G06T 2207/20081; G06T 2207/20084; G06T 2207/30168; G16H 30/40; G16H 30/20
See application file for complete search history.

(56) References Cited

U.S. PATENT DOCUMENTS

| | | | |
|---|---|---|---|
| 5,812,628 A | 9/1998 | Hsieh | |
| 6,517,488 B1 * | 2/2003 | Hossack | A61B 8/06 128/916 |

(Continued)

FOREIGN PATENT DOCUMENTS

| | | |
|---|---|---|
| WO | 2009017715 A1 | 2/2009 |
| WO | WO2012056379 A1 | 5/2012 |
| WO | 2016036516 A1 | 3/2016 |

OTHER PUBLICATIONS

U.S. Appl. No. 15/606,069, filed May 26, 2017.

(Continued)

*Primary Examiner* — Shefali D Goradia

(57) ABSTRACT

A medical scanner generates a medical image that may have an artifact. A machine-learnt detector, trained from a library of many different types of artifacts in images, detects any artifact in the medical image for a patient. The location of the artifact is highlighted, providing an indication of possible artifact where the image may otherwise appear to represent anatomy or pathology. A machine-learnt network may be applied to the medical image to determine a correction, such as different scan or reconstruction, to remove or reduce the artifact.

18 Claims, 2 Drawing Sheets

(51) Int. Cl.
*G06T 5/00* (2006.01)
*G16H 30/20* (2018.01)

(52) U.S. Cl.
CPC .............. *G06T 2207/30168* (2013.01); *G06T 2210/41* (2013.01); *G16H 30/20* (2018.01)

(56) References Cited

U.S. PATENT DOCUMENTS

| | | | | |
|---|---|---|---|---|
| 9,427,205 | B1* | 8/2016 | Chen | A61B 6/5258 |
| 9,569,736 | B1 | 2/2017 | Ghesu et al. | |
| 10,210,613 | B2* | 2/2019 | Xu | G06T 7/0012 |
| 2007/0015995 | A1* | 1/2007 | Lang | A61B 5/055 |
| | | | | 600/407 |
| 2010/0130863 | A1* | 5/2010 | Kelly | A61B 8/14 |
| | | | | 600/443 |
| 2010/0160768 | A1* | 6/2010 | Marrouche | A61B 6/503 |
| | | | | 600/420 |
| 2015/0250450 | A1* | 9/2015 | Thomas | A61B 8/4416 |
| | | | | 600/411 |
| 2016/0350620 | A1* | 12/2016 | Rao | G06K 9/6256 |
| 2016/0350919 | A1* | 12/2016 | Steigauf | G06T 7/0014 |
| 2017/0330319 | A1* | 11/2017 | Xu | G06T 7/0012 |

OTHER PUBLICATIONS

Mueen A et al.; "Automatic Multilevel Medical Image Annotation and Retrieval"; Journal of Digital Imaging; The Journal of the Society for Computer Applications in Radiology; Springer Verlag, NE; vol. 21; No. 3; Sep. 11, 2007; pp. 290-295.

Microsoft Research; "Research in Focus: Project InnerEye—Assistive AI for Cancer Treatment"; Youtube, Jul. 18, 2017; Retrieved from the Internet: URL:https://www.youtube.com/watch?v=jaFTXi56bFI: p. 1.

* cited by examiner

ARTIFACT IDENTIFICATION AND/OR CORRECTION FOR MEDICAL IMAGING

BACKGROUND

The present embodiments relate to medical imaging artifacts. Medical imaging is used for clinical diagnosis or prognosis. In medical imaging, the process of image acquisition, reconstruction, and/or rendering often introduces artifacts, causing the images to be of poor quality. One or more of different types of artifacts, such as motion blur, noise, streaking, intensity inhomogeneity, ripples, partial volume effects, or pseudo enhancements are in the generated image. An artifact may interfere with clinical evaluation, such as falsely mimic anatomy and/or providing false clinical indications (i.e., a pseudo enhancement artifact mimicking stroke or malignant lesion). Artifacts may result in patients having to be re-scanned, increasing costs, radiation to the patient, and time in the hospital. Artifacts may be overlooked or taken as "truth" in diagnosis.

The artifacts may be avoided by selection of protocol, patient positioning, and reconstruction algorithm. In many cases, these artifacts cannot be predicted due to the patient, system, or scanning variations.

Artifacts are typically identified by physicians, technologists, or radiologists. Based on experience, the presence or influence of an artifact is recognized. The identification of these artifacts is strongly based on personal experience and knowledge of artifacts, especially in specific imaging modalities.

SUMMARY

By way of introduction, the preferred embodiments described below include methods, systems, instructions, and non-transitory computer readable media for identification and/or correction of artifacts in medical images. A medical scanner generates a medical image that may have an artifact. A machine-learnt detector, trained from a library of many different types of artifacts in images, detects any artifact in the medical image for a patient. The location of the artifact is highlighted, providing an indication of possible artifact where the image may otherwise appear to represent anatomy or pathology. A machine-learnt network may be applied to the medical image to determine a correction, such as different scan or reconstruction, to remove or reduce the artifact.

In a first aspect, a method is provided for artifact identification in a scanner image from a medical scanner. The medical scanner generates a scanner image representing a patient. The scanner image has one or more artifacts due to the generating by the medical scanner. A machine-learnt detector trained from a library of artifact images is applied to the scanner image and detects locations of the one or more artifacts in the scanner image. The scanner image is displayed on a display device with the locations of the one or more artifacts highlighted.

In a second aspect, a system is provided for artifact identification in a medical image. A medical scanner is configured to scan a patient and form an image of the patient from the scan. An image processor is configured to identify an artifact in the image from application of a first machine-learnt network to the formed image. The first machine-learnt network is trained from samples with different types of artifacts. The image processor is also configured include an indication of the artifact on the image. A display is configured to display the image with the indication.

In a third aspect, a method is provided for correction of an imaging artifact from a medical scanner. The medical scanner generates a first image representing a patient. The image has an imaging artifact. A first machine-learnt network detects the imaging artifact in the first image. A second machine-learnt network determines a correction of the detected imaging artifact. The first image is re-generated as a second image using the correction. The second image is displayed.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

To improve identification of artifacts, a large database with prior knowledge of all or various known artifacts is used. Deep learning or other machine learning algorithms train a machine-learnt network to identify image artifacts automatically and in real-time at the scanner. The machine learning cycles through the clinically produced images to identify common and known patterns of artifacts and the corresponding image context.

The machine-learnt detector is applied to a medical image for a patient. Any artifact area in the patient's medical image is identified. For example, possible beam hardening, partial volume effects, or fan beam artifacts are detected. The user is alerted as to the presence of the artifact, allowing correction while the patient is at the scanner. Alternatively or additionally, the detection may be a way to "warn" readers or radiologists that a given location of the image may be a possible artifact rather than anatomy or pathology, allowing the reader or radiologist to take care in reading the image at that location. The image accuracy may be improved by alerting the user to the presence of more subtle artifacts.

Big-data information in a database, such as DICOM headers and clinical image images with and without artifacts, is used to train a machine network to provide corrections. In addition to identifying an artifact, one or more ways to correct the artifact are provided by the machine-learnt network. The prior knowledge in the database and experience in scanning, rendering, and/or reconstruction methods is used to correct the medical imaging. In the case of "correctable" artifacts, the workflow may be improved by correction while the patient is still available. The reliance on experienced users for artifact identification and correction may be reduced.

Figure 1:
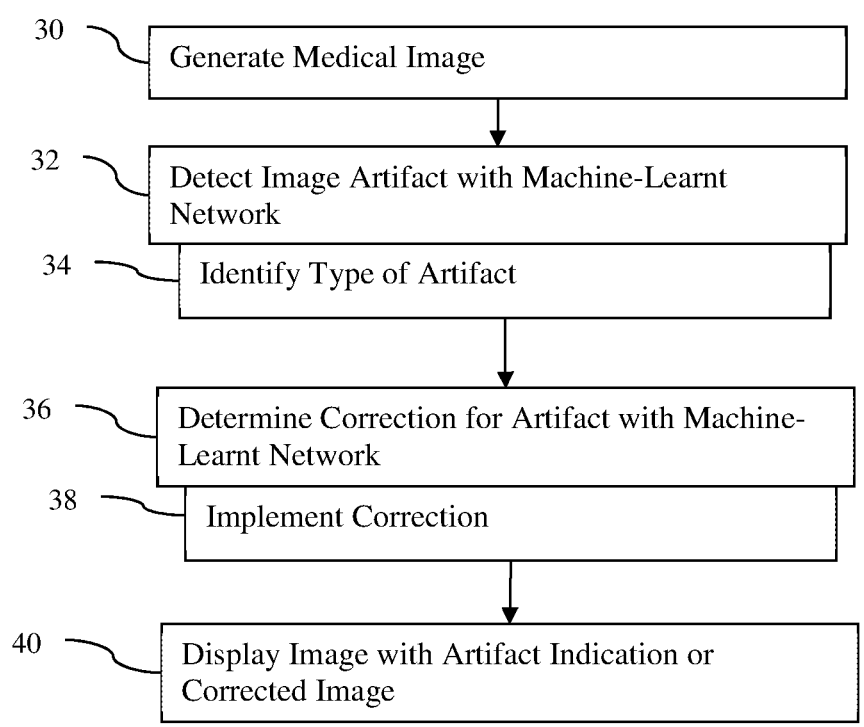
FIG. 1 shows one embodiment of a method for artifact identification and correction in medical imaging.

FIG. 1 shows one embodiment of a method for artifact identification and/or correction in a scanner image from a medical scanner. A machine-learnt detector is applied to a medical image for a patient. The detector is trained from a library of different examples of artifacts, such as a library of many different types of artifacts. Any artifacts in the medical image are detected and indicated on a display for use in diagnosis and/or prognosis from the image. A different machine-learnt network may be used to indicate a correction to remove or reduce the artifact. By applying the correction network and/or detector in real-time with or during a patient scan or patient appointment, the patient is available for any re-scanning. Machine-learnt detectors or networks may be applied in a matter of seconds, avoiding the longer times needed for programmed image processing to detect.

Additional, different, or fewer acts may be provided. For example, act 30 is replaced with loading a medical image from a picture archiving and communications system (PACS). As another example, acts 36 and/or 38 are not performed where artifacts are identified, but correction is not performed, or manual or expert-based correction is used. In yet another example, act 34 is not performed. The artifacts are identified by indicating the location, not the type of artifact.

Figure 3:
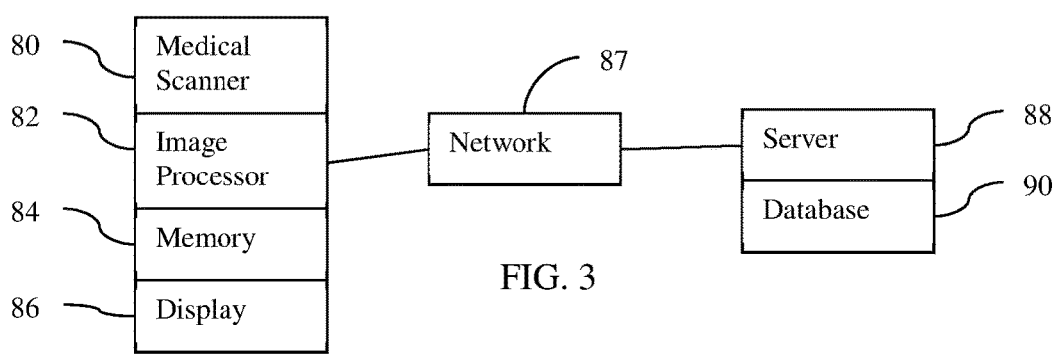
FIG. 3 is a block diagram of one embodiment of a system for artifact identification and/or correction in medical imaging.

The acts are performed by the system of FIG. 3, other systems, a medical scanner, a workstation, a PACS workstation, a computer, and/or a server. For example, act 30 is performed by a medical scanner. Acts 32-40 are performed by a processing component, such as the medical scanner (e.g., image processor of the scanner), a workstation, and/or a computer. The acts are performed in the order shown (e.g., top to bottom) or other orders.

In act 30, a medical scanner generates an image representing a patient. The image is made available by or within the medical scanner. The medical image or dataset is acquired by the medical scanner. The generated image is provided directly upon creation from or within the medical scanner. Upon completion of the scan and prior to the patient leaving the scan room, the image is generated. The image may be generated during the scanning session for the patient. The session is while the patient is in position to be scanned, in the scanning room, and/or during a scanning appointment. Alternatively, the medical scanner generates the image, and the image is stored, such as in a PACS system. This generated image is accessed by loading from the memory. Acquisition may be through transmission over a network.

The image is medical imaging data. The medical image is a frame of data representing the patient. The data may be in any format. While the terms image and imaging are used, the image or imaging data may be in a format prior to actual display of the image. For example, the medical image may be a plurality of scalar values representing different locations in a Cartesian or polar coordinate format different than a display format. As another example, the medical image may be a plurality red, green, blue (e.g., RGB) values output to a display for generating the image in the display format. The medical image may be currently or previously displayed image in the display or another format. The image or imaging is a dataset that may be used for imaging, such as scan data representing the patient.

Any type of medical image and corresponding medical scanner may be used. In one embodiment, the medical image is a computed tomography (CT) image acquired with a CT system. For example, a chest CT dataset may be used for detecting a bronchial tree, fissures, and/or vessels in the lung. For CT, the raw data from the detector is reconstructed into a three-dimensional representation. As another example, magnetic resonance (MR) data representing a patient is acquired. MR data is acquired with an MR system. The data is acquired using a pulse sequence for scanning a patient. Data representing an interior region of a patient is acquired. For MR, the magnetic resonance data is k-space data. Fourier analysis is performed to reconstruct the data from the k-space into a three-dimensional object or image space. The data may be ultrasound data. Beamformers and a transducer array scan a patient acoustically. The polar coordinate data is detected and processed into ultrasound data representing the patient. The data may be positron emission tomography (PET), single photon emission computed tomography (SPECT), or other nuclear imaging data. Radioactive emissions from within the patient are detected and reconstructed into imaging data. The data may be x-ray data, such as projection data acquired by detecting x-rays from a source after passing through a patient.

The medical image represents tissue and/or bone structure of the patient. Alternatively, the medical image represents flow, velocity, or fluids within the patient. In other embodiments, the medical image represents both flow and structure. For PET and SPECT, the scan data represents function of the tissue, such as uptake.

The medical image represents a one, two, or three-dimensional region of the patient. For example, the medical image represents an area or slice of the patient as pixel values. As another example, the medical image represents a volume or three-dimensional distribution of voxels. A three-dimensional volume may be represented as pixel values by rendering to a two-dimensional format. The medical image is acquired as a frame of data. The frame of data represents the scan region at a given time or period. Values are provided for each of multiple locations distributed in two or three dimensions. The dataset may represent the area or volume over time, such as providing a 4D representation of the patient.

The image is generated from scanning. Scan data representing the patient is acquired. The scan data is image processed to generate the image. Any image processing may be used, such as reconstruction, filtering, scan conversion, and/or three-dimensional rendering. The scanning and image processing use different optional operations and/or different settings of variables. The choice of settings or operational approaches may contribute more or less to artifacts. For example, one type of reconstruction may be less susceptible to generating artifacts than another type of reconstruction. As another example, some settings may result in the image processing being more susceptible to artifacts. Some image processing may be specifically applied to reduce artifacts.

The image may include one or more imaging artifacts. The process for creating the image from scanning to display may result in artifacts, which do not reflect the actual state of the patient. Different modalities of imaging are susceptible to different types of artifacts. The physics for scanning and/or the processing to create the image from the scan may generate an artifact. The reconstruction and/or rendering from three to two dimensions may create artifacts. Motion of the patient or sensor performing the scan may generate an artifact.

Example artifacts in medical imaging include noise, blur (e.g., motion artifact), shading (e.g., blockage or interference with sensing), under-sampling artifacts, streak, ripple, partial volume, and/or pseudo enhancements. Some artifacts may mimic anatomy and/or pathology. For example, partial volume artifacts are created in CT imaging where contrasting densities next to each other cause creation of values.

These partial volume effects may appear as a lesion or anatomical structure. Streaks in a given direction may mimic pathology or anatomy. In another example, high frequency signal may cause pseudo enhancement artifacts, such as where a dense bone region influences values in soft tissue. The pseudo enhancement artifact may appear as a lesion or stroke pathology.

Any level of artifact may exist. The scan settings for the medical scanner, condition of the patient, amount of movement, filtering, reconstruction, three-dimensional rendering to two-dimensional image, other image processing, and/or other factors may contribute to different levels of artifacts in an image. One image may include one type or multiple types of artifacts. The level may be a function of the severity (e.g., intensity or contrast) and/or extent (e.g., distribution or number of instances).

Figure 2:
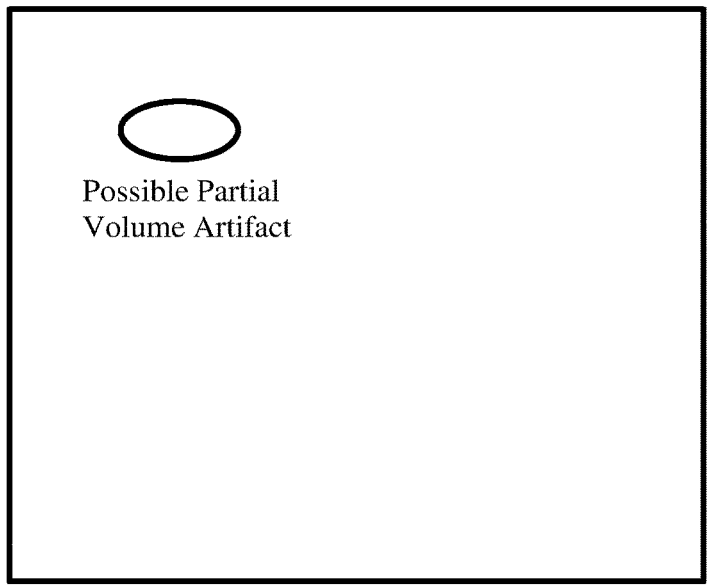
FIG. 2 illustrates one example indication of a detected artifact in a medical image.

In act 32, a machine detects one or more imaging artifacts in the medical image of the patient. The locations of possible imaging artifacts are detected. The locations may be a point, line, curve, area, or volume. The location may be a segmentation of the artifact or a general region that includes the artifact. For example, FIG. 2 shows an oval in which a possible artifact is detected. Rather than finding a center or shape of the artifact, a region surrounding the artifact is located. In the example of FIG. 2, one imaging artifact is detected. In other examples, none, two, or more imaging artifacts are detected.

The imaging artifacts are detected by application of a machine-learnt detector. Any machine capable of applying the machine-learnt detector may be used. For example, a computer, server, or image processor of the medical scanner inputs the image to learned matrices or a matrix learned as the machine-learnt detector and outputs locations of any imaging artifacts in response to the input. The learned matrix or matrices are a machine-learned network.

The machine-learnt detector is any type of machine-learnt detector that receives input features and outputs a detected artifact. Support vector machine, Bayesian network, a probabilistic boosting tree, neural network, sparse auto-encoding detector, or other now known or later developed machine learning may be used. Any semi-supervised, supervised, or unsupervised learning may be used. Hierarchal, cascade, or other approaches may be used.

In one embodiment, a neural network (e.g., deep neural network) is used. For deep-learnt networks, layers create increasingly abstract features from outputs of pervious layers. The resulting machine-trained detector is a matrix for inputs, weighting (e.g., convolution kernel), and combination to output a detection and/or probability of class membership. The deep machine-trained detector includes two or more layers relating the input to the class. In one embodiment, the trained model is a deep neural network with convolutional layers, fully connected layers, and/or pooling layers for feature reduction. Other layer arrangements may be used. Other deep learnt detectors may be trained and applied. The machine training is unsupervised in learning the features to use and how to classify given the learnt feature vector.

A machine trains the detector prior to application to an image of a patient. For example, a deep neural network is trained with a $L_2$ loss (e.g., least squares error) or other loss to obtain optimal network parameters. The difference between the ground truth for training images and the detection by the detector is minimized.

The detector is trained with training data. The training relates the input data to the detection through one or more layers. Samples of input data with ground truth are used to learn to detect artifacts. For deep learning, the detector learns the features of the input data to extract. In deep learning, the latent variables are learned by the machine training. Alternatively, the features, at least for the input, are manually programmed, such as filtering the scan data and inputting the results of the filtering.

The training data includes a library of medical images. Hundreds, thousands, or more samples are used. The medical images of the library are for a particular type of medical scanner. The library may be specific to a type of scanning or application (e.g., trained for upper torso CT or cardiac ultrasound). Alternatively, the library is for any application for a given type of medical scanner and/or for any type of medical scanner.

The training data includes ground truth information. An expert annotates each of the sample medical images to indicate any artifacts. For example, each artifact in each of the sample medical images is annotated in a same way as the desired output, such as a point, segmentation, and/or general region. The library may contain both artifact images and images without an artifact. Since large parts of artifact images may be free of an artifact, the library may be formed of only artifact images. The parts without artifacts may be used as samples free of artifacts.

The artifact images for training may include images of any type of artifact. Samples of one, two, or more types of artifacts are included. In one embodiment, samples of all the known artifacts for a particular hospital, practice, physician, type of scanner, application, or field are included. In other embodiments, samples of just the most common, the pathology or anatomy mimicking, or selected sub-set of all known types of artifacts are used. The artifact images of the library for training include different types of artifacts such that the detector learns to detect artifacts in general. Any of a group of different artifacts that exist in an image may be detected.

The detector is trained to detect artifacts based on the input medical image. For example, deep learning is performed. The input is the medical image. The detector learns features to extract from the image and learns to relate values of the features to the existence of an artifact. The learnt features from the deep learning are used for detecting artifacts. In additional or alternative embodiments, manually programmed features (e.g., Haar wavelets, steerable features, maximum detection) are extracted from the medical image as the input feature vector.

Other input features may be used in addition to features derived from the input medical image. For example, clinical data (e.g., family history, symptoms, test results, and/or diagnosis) is input or features derived therefrom are input. As another example, image generation settings, such as a DICOM header information or other collection of scan, filtering, reconstruction, and/or rendering settings, are used as input features.

The detector learns to detect the artifact as a binary indication. Each voxel or pixel is part of an artifact or not. Alternatively, a probability of the pixel being part of an artifact is predicted. The machine-trained features, kernels or layer values are used to compute the probability for each pixel being an artifact. The resulting probabilities may be clustered to identify each possible artifact in an image. Alternatively, the detector learns to detect artifacts over multiple pixels rather than pixel-by-pixel. The map is a spatial distribution of probability of artifact or not.

After creation, the machine-learnt detector includes one or more layers. For a manually programmed features, one layer is a network relating the features of the input vector or input vectors to the class (i.e., artifact or no artifact). For a deep-learnt network, at least one feature layer is learned from the training data rather than manually programmed. More than two layers may be provided, such as a neural network with three or more layers.

Once trained, the machine-learnt detector is applied to a medical image for a patient. The detector detects any possible artifacts in the medical image based on the knowledge learned through training. The input feature vector is populated, such as inputting the medical image with or without other input features (e.g., image generation settings). The values of the input feature vector are applied to the detector. The detector outputs the locations of any possible artifacts based on the machine-learnt knowledge from the library of training data.

The detection is performed during the scanning session. For example, the detection is performed while the patient is positioned for scanning by the medical scanner or still within the room with the medical scanner. The technician may view detected artifacts to determine whether to scan the patient again before the patient leaves the appointment. Where different image processing may be used, additional scanning of the patient may be avoided. This determination is made while the patient is still available in case another scan is needed.

The machine-learnt detector may be trained to indicate a type of artifact in act 34. In addition to detecting the location, the type of artifact is detected. For example, FIG. 2 shows detecting the general region of an artifact as well as the type. Since the machine-learnt detector is trained based on a library of sample artifact images with different types of artifacts, the ground truth labels of the type of artifact may be used to train for detection of the type.

One detector may detect both locations and types of different artifacts. Hierarchal or a cascaded detection may be used, such as detecting location and then detecting type. Different detectors may be applied. For example, different detectors are trained to detect different types of artifacts. In detecting the location by the detector for a specific type of artifact, both location and artifact type are provided. As another example, one detector detects location of any of different types of artifacts, and another detector detects the type. In yet another example, one detector detects the location of any of different types of artifacts, and different other detectors detect whether the artifact is of a particular type.

In one embodiment, the detector is trained as a multi-task detector. A cascade or hierarchy of detectors may be used instead of or as a multi-task detector. Any other class may be used for the multi-classification. In one approach, the machine identifies a type of artifact or types of artifacts with the location or existence of the artifact in act 32. For example, the detector locates an artifact as shown in FIG. 2 by the oval and identifies the artifact as a partial volume artifact as shown in FIG. 2 by the annotation. Separate locations and corresponding types of artifacts may be output. The severity and/or extent may be indicated as a class. Multi-task training adds multiple losses to obtain network parameters for multiple classes. In alternative embodiments, the type of artifact is not detected.

In act 36, the same or different machine as used in act 32 determines a correction of one or more of the detected imaging artifacts. The medical scanner, image processor, workstation, server, or other machine determines the correction for the artifact.

The correction is to remove or reduce the artifact. Some corrections may not reduce one artifact to reduce other artifacts. The location of the artifact may be used to determine whether to correct less or not where different artifacts are to be corrected by different amounts. Some corrections may correct less, but for a broader range of types of artifacts and/or locations. The correction may focus on one type or different types of artifacts depending on the application, physician, or other criterion.

To reduce or remove an artifact, the same scan data is re-processed, an image process is applied, and/or another scan is performed. For example, the artifact may be due to scan settings. The patient is scanned again with different settings. The different settings are the correction (i.e., change in scan settings). As another example, the artifact may be corrected by using different filtering, reconstruction, and/or three-dimensional rendering. The settings or approach used for any image process are changed as the correction. The previously acquired scan data is image processed again using the different settings. In other embodiments, the correction is application of further image processing, such as filtering to reduce or remove the artifact. The correction may alter the artifact so that the artifact is more obvious to the viewer and/or mimics pathology or anatomy less.

The correction may be based on the type of artifact to be corrected, on the combination of types of artifacts to be corrected, on the amount of correction to be provided, on the location or locations of the artifacts, on patient characteristics, and/or another criterion. The magnitude of the correction, type of correction, and/or another correction characteristic is determined based on one or more criteria.

To determine the correction, a machine-learnt network is applied. A different machine-learnt network than the detector determines the correction of one or more detected imaging artifacts. The machine-learnt network determines scan settings, reconstruction settings, rendering settings, different scan configurations, different reconstructions, different rendering, or combinations thereof.

The same or different type of machine-learnt network used for the detector is applied for correction. For example, a neural network is trained with deep learning. The layer structure of the neural network for correction is the same or different than used for detection. As another example, a probabilistic boosting tree is trained as the machine-learnt network. The machine-learnt network is any type of machine-learnt network that receives input features and outputs a classification (e.g., correction) based on machine training from samples with ground truth. Support vector machine, Bayesian network, a probabilistic boosting tree, neural network, sparse auto-encoding detector, or other now known or later developed machine learning may be used. Any semi-supervised, supervised, or unsupervised learning may be used. Hierarchal, cascade, or other approaches may be used.

Different input features are used for training the network for determining correction than used for detection of the artifacts. Some input features may be the same. For example, the image is input to both. As another example, the outputs of manually programmed convolution (e.g., Haar wavelets) with the image are used as inputs to both. Since the network is being machine trained to determine a correction, some of the input features relate to the settings. For example, the DICOM header or other information provide scan, reconstruction, rendering, and/or other image processing settings. Patient characteristics, such as clinical information (e.g., age, weight, or sex) may also be used as input features.

The training data includes ground truth corrections. The ground truth is the correction or corrections applied by experts given artifact images, such as the artifact images of the library used to train the machine-learnt detector. Given the scan and image processing settings, the change or changes to correct the imaging artifacts are used as the ground truth for determining the correction. The machine training learns to associate the input feature vector (e.g., image with artifacts or features derived therefrom, patient characteristics, and/or image generation settings) with the correction or corrections. Any error function and optimization may be used for learning the associations.

The samples of corrections may be specific to the type of imaging artifact. The training data used is specific to the type of artifact. One network is trained for one type of artifact. Given a type of artifact in an image, the appropriate machine-learnt network is selected and used to determine the correction. Alternatively, the network is trained to provide corrections for different types of artifacts using the training data associated with the different types of artifacts. The network may be trained to provide a correction appropriate for a combination of different types of artifacts in one image. The network is trained based on samples of corrections for the type of the imaging artifact or artifacts.

After creation, the machine-learnt network includes one or more layers. For a manually programmed features, one layer is a network relating the features of the input vector or input vectors to the correction class. For a deep-learnt network, at least one feature layer is learned from the training data rather than manually programmed. More than two layers may be provided, such as a neural network with three or more layers.

By application of the input feature vector or vectors, the machine-learnt network relates the values of the features to the correction or corrections. The correction classes are based on the training. The correction may be one or more settings for any imaging parameters (e.g., scan, filter, reconstruction, and/or rendering settings) or one or more different imaging processes. Where the corrections used for training include consideration of severity and/or extent of the artifacts, the correction output by the network corrects for the severity and/or extent.

In addition to outputting the correction, the network may output additional information. A probability of class membership may be output (e.g., 75% likelihood of correction A and 25% likelihood of correction B). The user or machine may select the correction (e.g., correction A) or apply both to view results.

The detector and/or the correction network are trained and used for specific circumstances. Different networks and/or discriminative detectors are provided for different circumstances. For example, the correction network and/or detector are specific to diagnosis, artifact, scan modality, tissue of interest, type of patient, or other environmental or clinical situation. In other embodiments, the correction network and/or detector are trained for and applied over a range of situations. For example, the same correction network and detector are used for any type of artifact in any tissue associated with a particular scan modality.

In act 38, the correction or corrections are implemented. In one embodiment, the use, viewer, or operator re-configures the image generation using the correction. The change or absolute setting provided by the correction is set in the medical scanner or workstation. A process to be applied as the correction (e.g., filtering) may be implemented.

In another embodiment, the correction or corrections are implemented by the machine, such as the medical scanner or workstation. At least part of the implementation is without user input. The correction is applied without the user configuring the medical scanner or workstation with the correction. Rather than the user setting the parameter values, the parameters are automatically populated. The user merely confirms and activates. Alternatively, the medical scanner or workstation implements the correction without any user input or control from determining the correction to presenting the corrected image on the display. Where the patient does not have to be repositioned and/or manual safety checks performed, the automatic implementation may occur free of user input.

The implementation of the correction re-generates the original artifact image as another image. The other image is generated using the correction. The same scan data may be used, but image processed differently. For example, a different reconstruction (e.g., type of reconstruction) is applied to the scan data to avoid or limit artifacts. As another example, a different transfer function in three-dimensional rendering is used. In other examples, the same type of reconstruction or transfer function is applied, but with one or more values of variables being different.

For obvious and/or preventable artifacts (e.g., beam hardening or partial volume effects), new scan protocols are proposed or used automatically to reprocess with specific reconstruction algorithms. For example, a different reconstruction protocol may reduce the artifacts due to metal objects in the patient in CT imaging. For more subtle artifacts that mimic pathology or anatomy, the artifacts may be highlighted for review and, if the user indicates the existence of the artifact, a correction is determined and implemented.

In act 40, a display device displays an image. To display the image, the image is transmitted to a display plane memory within the medical system or workstation. Alternatively, the image is transmitted to a remote memory or display over a local or wide area network.

The image may be the original image with indications of one or more artifacts. The artifacts are highlighted so that the artifacts are more likely discernable to the viewer for deciding whether the image is sufficient and/or to avoid reliance on an artifact in diagnosis or prognosis. Prior to the image or images being evaluated, the highlighting is added.

The highlighting is an indication of the artifact or artifacts. Any highlighting may be used, such as a label with or on the image indicating that artifacts exist in the image. The location of the artifacts is not indicated. The highlighting may be more specific, such as a graphic (e.g., marker or border trace) indicating the location of the artifact. The highlighting may be an annotation, such as the type of artifact displayed next to the location of the artifact. FIG. 2 shows an example display of a medical image with a graphic marker (e.g., oval) and annotation (e.g., label of type of artifact) overlaid or incorporated into the displayed image. Each possible artifact is highlighted. Tinting or coloring may be used, such as coloring the artifacts. Different types of artifacts may be colored differently.

By displaying an image from a medical scanner with locations of one or more artifacts mimicking pathology or anatomy highlighted, the user may consider the likelihood of the artifacts in those locations in diagnosis or prognosis. The user may decide that actual anatomy or pathology, not an artifact, is represented. The user may decide the location is an artifact.

In another embodiment, the corrected image is displayed. Any artifacts in the corrected image may be detected and highlighted. Alternatively, the corrected image is displayed without detecting artifacts. The corrected image may be free of artifacts due to the correction.

The display of the image with highlighting and/or corrected image occurs during the imaging session. Prior to being evaluated for clinical diagnosis and/or prognosis, the image is displayed. The technician and/or physician may review the image for sufficiency or diagnosis while the patient is within the room or facility (e.g., during the scan appointment). If needed, the patient is still available for re-scanning as a correction. The image may be displayed while the patient is still on or in the medical scanner and/or positioned for scanning. The detection and highlighting or the correction allows the image to be assessed for accurate representation of the patient. In alternative embodiments, the image is displayed after the imaging session is complete. The highlighting is used to assist in prognosis or diagnosis decisions even if the patient is not available for immediate re-scanning.

FIG. 3 shows one embodiment of a system for artifact identification and/or correction in a medical image. The system is used for machine training and/or application of a machine-learnt network. The machine learning and learnt network or networks are for detecting artifacts in an image and/or determining corrections to reduce or remove detected artifacts. For example, the method of FIG. 1 is applied by the components of the system.

The system is distributed between the medical scanner 80 and a remote server 88. In other embodiments, the system is just the server 88 or just the medical scanner 80 without the network 87. In yet other embodiments, the system is a computer or workstation instead of the medical scanner 80, instead of the server 88, or instead of both.

The system includes a medical scanner 80, an image processor 82, a memory 84, a display 86, a communications network 87, a server 88, and a database 90. Additional, different, or fewer components may be provided. For example, network connections or interfaces are provided, such as for networking with a medical imaging network or data archival system. In another example, a user interface is provided. As another example, the server 88 and database 90 are not provided, or only the server 88 and database 90 are provided. In other examples, the server 88 connects through the network 87 with many imaging systems 80 and/or image processors 82.

The image processor 82, memory 84, and display 86 are part of the medical scanner 80. Alternatively, the image processor 82, memory 84, and display 86 are part of an archival and/or image processing system, such as associated with a medical records database workstation or server, separate from the medical scanner 80. In other embodiments, the image processor 82, memory 84, and display 86 are a personal computer, such as desktop or laptop, a workstation, or combinations thereof. The image processor 82, display 86, and memory 84 may be provided without other components for acquiring data by scanning a patient.

The medical scanner 80, image processor 82, memory 84 and display 86 are provided at a same location. The location may be a same room, same building, or same facility. These devices are local relative to each other and are remote to the server 88. The server 88 is spaced apart by the network 87 by being in a different room or facility or by being in a different city, county, state, or country. The server 88 and database 90 are remote from the location of the image processor 82 and/or medical scanner 80.

The medical scanner 80 is a medical diagnostic imaging system. Ultrasound, computed tomography (CT), x-ray, fluoroscopy, positron emission tomography (PET), single photon emission computed tomography (SPECT), and/or magnetic resonance (MR) systems may be used. The medical scanner 80 may include a transmitter and includes a detector for scanning or receiving data representative of the interior of the patient. The medical scanner 80 is configured by settings to scan a patient and form an image of the patient from the scan.

In one embodiment, the medical scanner 80 is a CT system. An x-ray source is connected with a gantry. A detector is also connected with a gantry opposite the x-ray source. The patient is positioned between the source and detector. The source and detector are on opposite sides of the patient and rotate and/or translate about the patient. The detected x-ray energy passing through the patient is converted, reconstructed or transformed into data representing different spatial locations within the patient.

In another embodiment, the medical scanner 80 is a MR system. The MR system includes a main field magnet, such as a cryomagnet, and gradient coils. A whole-body coil is provided for transmitting and/or receiving. Local coils may be used, such as for receiving electromagnetic energy emitted by atoms in response to pulses. Other processing components may be provided, such as for planning and generating transmit pulses for the coils based on the sequence and for receiving and processing the received k-space data. The received k-space data is converted into object or image space data with Fourier processing.

The memory 84 may be a graphics processing memory, a video random access memory, a random-access memory, system memory, cache memory, hard drive, optical media, magnetic media, flash drive, buffer, database, combinations thereof, or other now known or later developed memory device for storing data or image information. The memory 84 is part of the medical scanner 80, part of a computer associated with the image processor 82, part of a database, part of another system, a picture archival memory, or a standalone device.

The memory 84 stores medical imaging data representing the patient, weights or values of parameters making up some of the layers of the machine-learnt detector, outputs from different layers, one or more machine-learnt matrices, and/or images. The memory 84 may store data during processing for application and/or may store training data (e.g., images and scores).

The memory 84 or other memory is alternatively or additionally a non-transitory computer readable storage medium storing data representing instructions executable by the programmed image processor 82 for training or use of one or more machine-learnt networks in medical imaging. The instructions for implementing the processes, methods and/or techniques discussed herein are provided on non-transitory computer-readable storage media or memories, such as a cache, buffer, RAM, removable media, hard drive or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The image processor 82 is a general processor, central processing unit, control processor, graphics processing unit, digital signal processor, three-dimensional rendering processor, application specific integrated circuit, field programmable gate array, digital circuit, analog circuit, combinations thereof, or other now known or later developed device for training or applying machine-learnt networks in medical imaging. The image processor 82 is a single device or multiple devices operating in serial, parallel, or separately. The image processor 82 may be a main processor of a computer, such as a laptop or desktop computer, or may be a processor for handling some tasks in a larger system, such as in the medical scanner 80. The image processor 82 is configured by instructions, design, firmware, hardware, and/or software to perform the acts discussed herein.

The image processor 82 is configured to perform the acts discussed above for training or application. For training, the image processor 82 performs machine training using training data from the memory 84 and/or the database 90. For application, the image processor 82 uses a stored matrix or stored matrices for the machine-learnt network or networks. Values of input features are acquired and applied to the machine-learnt network or networks.

In one embodiment, the image processor 82 applies a machine-learnt detector to an image of a patient. The application of the machine-learnt network to the formed image identifies any possible artifacts in the image. The machine-learnt network is trained to identify different types of artifacts. For example, a deep neural network identifies different types of imaging artifacts.

In another embodiment, the image processor 82 applies a machine-learnt network to determine a correction for removing or reducing the artifact. The application of the machine-learnt network determines one or more corrections, such as scan or imaging processing settings. The machine-learnt network is trained to determine corrections for one or more types of artifacts and/or combinations of artifacts.

The correction may be indicated on the image. For example, the artifact image is displayed adjacent to the corrected image. As another example, the act of correction and/or the correction settings are displayed. The proposed settings may be displayed for confirmation by the operator, or the settings used to correct may be displayed to inform the operator.

The image processor 82 is configured to generate the image to be displayed, such as overlaying graphics or other indications on the medical image. The location of each artifact is shown. The image processor 22 adds the indication to the image. Any identified artifacts are indicated on the image. The existence of one or more artifacts is indicated. Alternatively, each identified artifact is indicated by a graphic, coloring, annotation, marker, or other highlighting. The image processor 82 transmits the image for display over the network 87, to the display 86, or to the memory 84. The processor 82 may be configured to generate a user interface for receiving corrections or verification of artifact identity.

In one embodiment, the image processor 82 receives feed back from application. The radiologist or other viewer indicates when an indicated artifact is or is not an actual artifact. This feedback may be used as training data. As the detection is confirmed for each case, the results are collected or added to the library. The machine learning may be applied again using the larger library. Alternatively, incremental or on-going machine learning is applied to update the network based on the further samples with ground truth.

The display 86 is a monitor, LCD, projector, plasma display, CRT, printer, or other now known or later developed devise for outputting visual information. The display 86 receives images, graphics, text, annotations, highlighting, or other information from the image processor 82, memory 84, medical scanner 80, and/or server 88. One or more medical images are displayed. The images are of a region of the patient. The image includes an indication, such as a graphic or colorization, of the detected possible artifacts and/or types of artifacts. Corrections may be displayed without a medical image representation of the patient.

The network 87 is a local area, wide area, enterprise, another network, or combinations thereof. In one embodiment, the network 87 is, at least in part, the Internet. Using TCP/IP communications, the network 87 provides for communication between the image processor 82 and the server 88. Any format for communications may be used. In other embodiments, dedicated or direct communication is used.

The server 88 is a processor or group of processors. More than one server 88 may be provided. The server 88 is configured by hardware, firmware, and/or software. In one embodiment, the server 88 performs machine learning with training data in the database 90. The machine-learnt matrices are provided to the image processor 82 for application. The user-confirmed detections may be received from the image processor 82 for use in further training. Alternatively, the server 88 performs the application on an image received from the medical scanner 80 and provides the detected artifact location, artifact type, correction, and/or corrected image to the medical scanner 80.

The database 90 is a memory, such as a bank of memories, for storing training data, such as images and respective scores. Weights or values of parameters of the correction network and/or detector are stored in the database 90 and/or the memory 84.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for artifact identification in a scanner image from a medical scanner, the method comprising:
   generating, by the medical scanner, the scanner image representing a patient, the scanner image having one or more artifacts due to the generating by the medical scanner;
   detecting, by a machine-learnt detector trained from a library of artifact images, the machine-learnt detector applied to the scanner image, locations of the one or more artifacts in the scanner image; and
   displaying the scanner image on a display device with the locations of the one or more artifacts highlighted,
   wherein detecting comprises detecting the location and type of the one or more artifacts, and wherein displaying comprises displaying with the location highlighted and annotation of the type of each of the one or more artifacts.

2. The method of claim 1 wherein generating comprises generating computed tomography, x-ray, magnetic resonance, ultrasound, positron emission tomography, or single photon emission computed tomography image.

3. The method of claim 1 wherein generating comprises generating a two-dimensional representation of pixels or a three-dimensional set of voxels as the image.

4. The method of claim 1 wherein generating comprises generating with a partial volume effect or pseudo enhancement artifact as the one or more artifacts.

5. The method of claim 1 wherein generating comprises generating with the one or more artifacts mimicking pathology and/or anatomy of the patient, and wherein displaying comprises displaying the scanner image with the locations of the one or more artifacts mimicking pathology and/or anatomy highlighted.

6. The method of claim 1 wherein detecting comprises detecting with the machine-learnt detector comprising a deep-learnt neural network.

7. The method of claim 1 wherein detecting comprises detecting with the machine-learnt detector trained from the library, the artifact images of the library having different types of artifacts such that the detecting is of the different types of artifacts.

8. The method of claim 7 wherein the different types of artifacts include four or more of the types comprising streak, ripple, partial volume, pseudo enhancement, noise, blur, shading, and under-sampling artifacts.

9. The method of claim 1 wherein generating comprises scanning the patient during a scanning session, wherein detecting comprises detecting during the scanning session, and wherein displaying comprises displaying during the scanning session.

10. The method of claim 1 wherein detecting comprises detecting the location and type of the one or more artifacts, and further comprising determining a correction based on the type of the one or more artifacts, the correction determined by a machine-learnt network.

11. The method of claim 10 further comprising implementing the correction, at least in part, without user input.

12. The method of claim 1 wherein displaying comprises displaying with the locations designated by a graphic or annotation in the scanner image.

13. A system for artifact identification in a medical image, the system comprising:
a medical scanner configured to scan a patient and form an image of the patient from the scan;
an image processor configured to identify an artifact in the image from application of a first machine-learnt network to the formed image, the first machine-learnt network trained from samples with different types of artifacts, and the image processor configured to include an indication of the artifact on the image;
a display configured to display the image with the indication,
wherein configured to identify comprises detecting a location and type from the different types of artifacts, and wherein configured to display comprises displaying with the location highlighted and annotation of the type from the different types of artifacts.

14. The system of claim 13 wherein the first machine-learnt network comprises a deep neural network.

15. The system of claim 13 wherein the image processor is further configured to determine a correction for the artifact by application of a second machine-learnt network, and wherein the indication includes the correction.

16. A method for correction of an imaging artifact from a medical scanner, the method comprising:
generating, by the medical scanner, a first image representing a patient, the image having the imaging artifact;
detecting, by a first machine-learnt network the imaging artifact in the first image;
determining, by a second machine-learnt network, a correction of the detected imaging artifact;
re-generating the first image as a second image, the re-generating using the correction; and
displaying the second image,
wherein detecting comprises detecting the location and type of the one or more artifacts, and wherein displaying comprises displaying with the location highlighted and annotation of the type of each of the one or more artifacts.

17. The method of claim 16 wherein detecting comprises detecting a type of the imaging artifact, and wherein determining comprises determining with the second machine-learnt network trained based on samples of corrections for the type of the imaging artifact.

18. The method of claim 16 wherein re-generating comprises automatically reconstructing from scan data from the generating, the reconstructing being different than used for generating the first image.

* * * * *